(12) United States Patent
Wood et al.

(10) Patent No.: US 9,498,384 B2
(45) Date of Patent: Nov. 22, 2016

(54) ASSEMBLED INTERMEDIATE COMPRISING STAPLE FIBER NONWOVEN WEB AND ARTICLES

(76) Inventors: Leigh E. Wood, Woodbury, MN (US); Lori-Ann S. Prioleau, St. Paul, MN (US); Kerstin Ehlers, Langenfeld (DE); Bernard Vincent, Rueil Malmaison (FR)

( * ) Notice: Subject to any disclaimer, the term of this patent is extended or adjusted under 35 U.S.C. 154(b) by 17 days.

(21) Appl. No.: 13/308,996

(22) Filed: Dec. 1, 2011

(65) Prior Publication Data
US 2013/0143020 A1    Jun. 6, 2013

(51) Int. Cl.
| A61F 13/02 | (2006.01) |
| B32B 5/26 | (2006.01) |
| B32B 3/30 | (2006.01) |
| D04H 1/54 | (2012.01) |
| A61F 13/15 | (2006.01) |
| A61F 13/537 | (2006.01) |

(52) U.S. Cl.
CPC ......... *A61F 13/0206* (2013.01); *A61F 13/022* (2013.01); *A61F 13/15* (2013.01); *A61F 13/537* (2013.01); *A61F 13/53708* (2013.01); *B32B 3/30* (2013.01); *B32B 5/26* (2013.01); *D04H 1/54* (2013.01); *Y10T 442/69* (2015.04)

(58) Field of Classification Search
CPC .................. A61F 13/53704; A61F 13/53752; A61F 13/537–13/5376; A61F 2013/53765–2013/53795; A61F 13/0206; A61F 13/022; A61F 13/53708; D04H 1/54; A47L 13/00; A47L 25/00; Y10T 442/69; B32B 5/14–5/145

USPC .............. 442/327–417; 604/358–402
See application file for complete search history.

(56) References Cited

U.S. PATENT DOCUMENTS

| 2,399,258 | A | 4/1946 | Taylor |
| 2,399,259 | A | 4/1946 | Taylor |
| RE24,906 | E | 12/1960 | Ulrich |
| 3,537,121 | A | 11/1970 | McAvoy |
| 3,562,079 | A | 2/1971 | Steel |
| 3,686,049 | A | 8/1972 | Manner |
| 3,687,759 | A | 8/1972 | Werner |
| 3,691,004 | A | 9/1972 | Werner |
| 3,837,988 | A | 9/1974 | Hennen |
| 4,227,350 | A | 10/1980 | Fitzer |

(Continued)

FOREIGN PATENT DOCUMENTS

| CN | 201921003 U | 8/2011 |
| EP | 1504739 | 2/2005 |

(Continued)

OTHER PUBLICATIONS

Hydrophilic; Textile Glossary, Celanese Acetate, copyright 2001.*

(Continued)

*Primary Examiner* — Jennifer A Steele

(57) ABSTRACT

An assembled intermediate is described comprising a fluid transport element proximate an absorbent material is described. The fluid transport element comprises a thermoplastic nonwoven web comprising a plurality of bonded staple fibers having an average diameter of 20 to 500 microns and the web has a thickness of 3 to 20 mm, a density ranging from 0.01 to 0.10 g/cm³, and a work of compression no greater than 20 kJ/m³. Also described are articles comprising such assembled intermediate.

18 Claims, 5 Drawing Sheets

(56) References Cited

U.S. PATENT DOCUMENTS

| | | | |
|---|---|---|---|
| 4,351,683 A | 9/1982 | Kusilek | |
| 4,610,678 A | 9/1986 | Weisman | |
| 4,769,022 A | 9/1988 | Chang | |
| 4,834,735 A | 5/1989 | Alemany | |
| 4,988,344 A | 1/1991 | Reising | |
| 4,988,345 A | 1/1991 | Reising | |
| 5,019,065 A | 5/1991 | Scripps | |
| 5,047,023 A | 9/1991 | Berg | |
| 5,134,007 A | 7/1992 | Reising | |
| 5,147,345 A | 9/1992 | Young | |
| 5,296,289 A | 3/1994 | Collins | |
| 5,364,382 A * | 11/1994 | Latimer et al. | 604/378 |
| 5,439,458 A | 8/1995 | Noel | |
| 5,464,491 A | 11/1995 | Yamanaka | |
| 5,486,166 A | 1/1996 | Bishop | |
| 5,626,571 A | 5/1997 | Young | |
| H1698 H | 11/1997 | Lloyd | |
| 5,700,254 A | 12/1997 | McDowall | |
| 5,846,230 A | 12/1998 | Osborn, III | |
| 5,853,402 A | 12/1998 | Faulks | |
| 5,861,074 A | 1/1999 | Wu | |
| 5,874,160 A | 2/1999 | Keck | |
| 5,879,343 A | 3/1999 | Dodge, III | |
| 5,895,379 A | 4/1999 | Litchholt | |
| 5,913,850 A * | 6/1999 | D'Alessio et al. | 604/378 |
| 5,961,506 A | 10/1999 | Guidotti | |
| 5,968,855 A | 10/1999 | Perdelwitz | |
| 6,037,518 A * | 3/2000 | Guidotti et al. | 604/378 |
| 6,096,015 A | 8/2000 | Yeo | |
| 6,232,250 B1 | 5/2001 | Palumbo | |
| 6,241,714 B1 | 6/2001 | Raidel | |
| 6,246,776 B1 | 6/2001 | Merz | |
| 6,264,776 B1 * | 7/2001 | DiPalma | 156/73.1 |
| 6,312,545 B1 | 11/2001 | Nickel | |
| 6,372,952 B1 | 4/2002 | Lash | |
| 6,413,338 B1 | 7/2002 | DiPalma | |
| 6,417,427 B1 | 7/2002 | Roxendal | |
| 6,441,268 B1 | 8/2002 | Edwardsson | |
| 6,509,513 B2 | 1/2003 | Glaug | |
| 6,515,195 B1 | 2/2003 | Lariviere | |
| 6,528,439 B1 | 3/2003 | Stokes | |
| 6,673,982 B1 | 1/2004 | Chen | |
| 6,689,933 B1 | 2/2004 | DiPalma | |
| 6,700,034 B1 | 3/2004 | Lindsay | |
| 6,723,892 B1 | 4/2004 | Daley | |
| 6,762,139 B2 | 7/2004 | Strommen | |
| 6,808,664 B2 | 10/2004 | Falk | |
| 6,844,482 B2 | 1/2005 | Eliasson | |
| 6,896,669 B2 | 5/2005 | Krautkramer | |
| 7,138,561 B2 | 11/2006 | Fuchs | |
| RE39,919 E | 11/2007 | Dodge, II | |
| 7,429,689 B2 * | 9/2008 | Chen et al. | 604/378 |
| 7,491,354 B2 | 2/2009 | Andersen | |
| 2002/0010448 A1 | 1/2002 | Yoshimasa | |
| 2002/0022694 A1 | 2/2002 | Wallenwein | |
| 2004/0243078 A1 | 12/2004 | Guidotti | |
| 2005/0033253 A1 | 2/2005 | Fuchs | |
| 2006/0020250 A1 * | 1/2006 | Chester et al. | 604/378 |
| 2006/0094320 A1 | 5/2006 | Chen | |
| 2006/0135026 A1 | 6/2006 | Arendt | |
| 2006/0206073 A1 | 9/2006 | Crane | |
| 2007/0038195 A1 * | 2/2007 | Fuchs | A61F 13/53747 604/366 |
| 2008/0001431 A1 | 1/2008 | Thompson | |
| 2008/0132136 A1 * | 6/2008 | Uematsu et al. | 442/414 |
| 2010/0255258 A1 | 10/2010 | Curro | |
| 2010/0291213 A1 | 11/2010 | Berrigan | |
| 2010/0292664 A1 | 11/2010 | Marin | |
| 2010/0331804 A1 | 12/2010 | Larsson | |
| 2013/0143019 A1 | 6/2013 | Wood | |
| 2013/0143462 A1 | 6/2013 | Wood | |

FOREIGN PATENT DOCUMENTS

| | | |
|---|---|---|
| EP | 2058424 | 5/2009 |
| GB | 2331937 | 6/1999 |
| JP | 60-013511 | 1/1985 |
| WO | WO 93/11726 | 6/1993 |
| WO | WO 96/37644 | 11/1996 |
| WO | WO 03/015914 | 2/2003 |
| WO | WO 2004/020710 | 3/2004 |
| WO | WO 2004/020711 | 3/2004 |
| WO | WO 2009/008788 | 1/2009 |
| WO | WO 2010/056835 | 5/2010 |

OTHER PUBLICATIONS

International Search Report PCT/US2012/065801, Apr. 8, 2013, 3 pgs.

* cited by examiner

ASSEMBLED INTERMEDIATE COMPRISING STAPLE FIBER NONWOVEN WEB AND ARTICLES

SUMMARY

An assembled intermediate comprising a fluid transport element proximate an absorbent material is described. The fluid transport element comprises a thermoplastic nonwoven web comprising a plurality of bonded staple fibers having an average diameter of 20 to 500 microns and the web has a thickness of 3 to 20 mm, a density ranging from 0.01 to 0.10 g/cm$^3$, and a work of compression no greater than 20 kJ/m$^3$.

Also described are absorbent articles, comprising the assembled intermediate described herein, proximate an absorbent material, with the proviso that the absorbent article is not a personal hygiene article. The absorbent article may be suitable for use for spill containment or medical uses, such as wound dressings.

DETAILED DESCRIPTION

Figure 1:
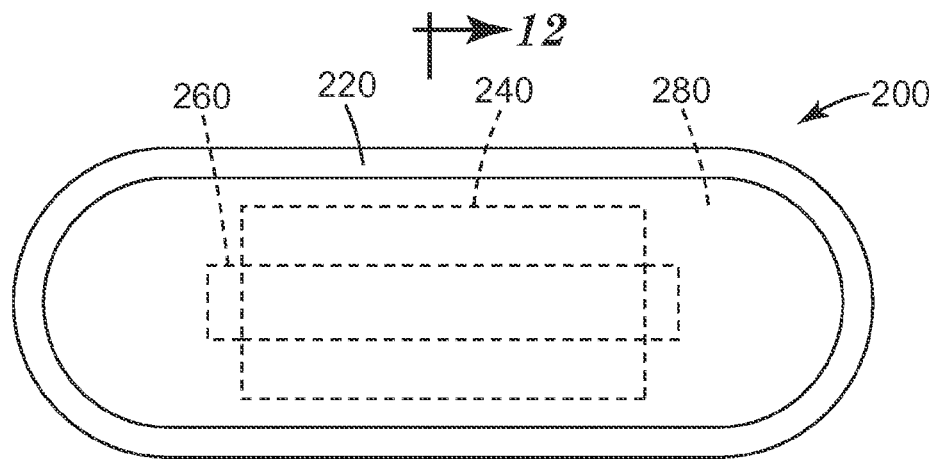
FIG. 1 is a top view of an absorbent article.

Presently described are assembled intermediates comprising a (e.g. air-laid) staple fiber web proximate an absorbent material. The assembled intermediates may be suitable for use in personal hygiene articles or other absorbent articles. Also described are absorbent articles suitable for use for spill containment or medical uses, such as wound dressings, comprising the assembled intermediate. Such absorbent articles are not personal hygiene articles, such as adult incontinent products, sanitary napkins, and disposable diapers.

The fibers of the web are formed from and thus comprise a thermoplastic polymer. Examples of suitable thermoplastic polymers that can be used to form the fibers or components thereof include polymers selected from the following classes: polyolefins, such as polyethylenes, polypropylenes, polybutylenes, blends of two or more of such polyolefins, and copolymers of ethylene and/or propylene with one another and/or with small amounts of polymerizable, higher, alpha olefins, such as pentene, methylpentene, hexane, or octane; halogenated polyolefins, such as chlorinated polyethylene, poly(vinylidene fluoride), poly (vinylidene chloride), and plasticized poly(vinyl chloride); polyester (polyethylene terephthalate ("PET") and copolyester-ether elastomers of cyclohexane dimethanol, tetramethylene glycol, and terephthalic acid; copolyester elastomers such as block copolymers of polybutylene terephthalate and long chain polyester glycols; polyethers, such as polyphenylene oxide; polyamides, such as poly(hexamethylenedipamide), e.g., nylon 6 and nylon 6,6; nylon elastomers; such as nylon 11, nylon 12, nylon 6,10 and polyether block polyamides; polyurethanes; copolymers of ethylene, or ethylene and propylene, with (meth)acrylic acid or with esters of lower alkanols and ethylenically-unsaturated carboxylic acids, such as copolymers of ethylene with (meth) acrylic acid, vinyl acetate, methyl acrylate, or ethyl acrylate; ionomers, such as ethylene-methacrylic acid copolymer stabilized with zinc, lithium, or sodium counterions; acrylonitrile polymers, such as acrylonitrile-butadiene-styrene copolymers; acrylic copolymers; chemically-modified polyolefins, such as maleic anhydride- or acrylic acid-grafted homo- or co-polymers of olefins and blends of two or more of such polymers, such as blends of polyethylene and poly(methyl acrylate), blends of ethylene-vinyl acetate copolymer and ethylene-methyl acrylate; and blends of polyethylene and/or polypropylene with poly(vinyl acetate). The foregoing polymers are normally solid, generally high molecular weight, and melt-extrudable such that they can be heated to form molten viscous liquids which can be pumped as streams to the extrusion die assembly and readily extruded therefrom under pressure as continuous filaments that are then cut into staple fibers.

Preferably the fibers are tough, durable, melt-bondable, thermoplastic, fibers comprising synthetic organic plastic polymer or blends or multi-component polymer fibers. In some embodiments, the filaments of the web comprise the same synthetic organic plastic material. In some embodiments, the fibers are formed from semi-crystalline thermoplastic polymers, such as polyolefins. In other embodiments, a portion of the filaments comprise one type of synthetic organic plastic material and a portion of the filaments comprise a different type of synthetic organic plastic material. The filament can comprise a plurality, e.g., 2 to 5, of components such as bi-component fibers, such as a sheath-core or side-by-side fibers. The plastics forming the fibers can further have incorporated adjuvants or additives to enhance a property of or impart a property to the filament, such as stabilizers, processing aids, fillers, coloring pigments, crosslinking agents, foaming agents, and fire retardants.

The staple fiber web may further comprise natural fibers in combination with fibers comprising synthetic organic plastic polymers.

Generally the fibers of the web have an average width, diameter, or cross-section dimension of at least 5, 10, 15, or 20 microns. The average diameter may range up to 1000 microns (1 mm), yet is typically no greater than 800 microns, or 700 microns, or 600 microns, and in some embodiments no greater than 500 microns or 400 microns. In some embodiments, the average diameter of the fibers of the web is no greater than 300, 250, 200, 150, 100, 75 or 50 microns. Smaller diameter staple fiber webs can provide improved flexibility (e.g. a lower work of compression). The filament cross sectional dimension (and shape of the cross section) is preferably substantially, or essentially, uniform along the length of the filament, e.g., uniformly round. The surface of the filament is typically smooth. The fibers can be in the shape or form of fibers, strips, or other narrow and long shapes. Aggregations can be made up of a plurality of fibers with the same or different plastic compositions, geometric shapes, sizes, and/or diameters. The fibers are typically solid. The fibers can be circular or round in cross section or non-circular in cross section, e.g., lobal, elliptical, rectangular, triangular, and shapes with radial arms such as "x-shaped". Unlike fiber made from melt-extrusion processes (e.g. spunbond or melt blown) that typically are continuous in length, the length of the staple fibers (i.e. fibers) is typically at least 1, 2, or 3 cm, and commonly no greater than 15 cm. In some embodiments, the length of the fibers is no greater than 10, 9, 8, or 7 cm.

Staple fiber webs can be made by various processes described in the art, such as air-laid and wet-laid process. In the wet-laying process, bundles of small fibers are separated and entrained in a liquid supply and then deposited onto a forming screen, usually with the assistance of a vacuum supply. Water is typically the preferred liquid. The randomly deposited fibers may by further entangled (e.g. hydro-entangled), or may be bonded to one another using, for example, thermal point bonding, autogeneous bonding, hot air bonding, ultrasonic bonding, needle punching, calendering, application of a spray adhesive, and the like.

In the air-laying process, bundles of small fibers are separated and entrained in an air supply and then deposited onto a forming screen, usually with the assistance of a vacuum supply. The randomly oriented fibers may then be bonded to one another using, for example, thermal point bonding, autogenous bonding, hot air bonding, needle punching, calendering, a spray adhesive, and the like. Illustrative air-laying process are taught in, for example, in U.S. Pat. No. 6,808,664 and U.S. Pat. No. 7,491,354; incorporated herein by reference. Such patents describe a forming box having spike rollers that blend and mix the fibers while gravity allows the fibers to fall down through an endless belt screen and form a web of interengaged fibers. A commercially available air-laid web forming apparatus is "RandoWebber" web forming machine, available from Rando Machine Corporation, Macedon, N.Y. This type of air-laying equipment uses circulating, forced air to randomize and interengage the input staple fibers. Air-laid nonwoven webs can be more efficient to manufacture than wet-laid nonwoven webs.

Each of these methods can generally forms a three-dimensional network of randomly orientated and interlaced fibers bonded together at points where the fibers cross and contact each other. "Randomly oriented" refers to a population of fibers wherein the fiber are not substantially aligned in a single direction.

In some embodiments, the thermoplastic staple fibers of the web may be thermally bonded to each other. Thermally bonded polyester fibers are described in 4,769,022; incorporated herein by reference. Preferably, the staple fibers are bonded with a binder comprising a "soft", "tough" binder (e.g. having a Knoop hardness of less than 3, such as a polyurethane binder. Various other binders are described in WO2010/056836; incorporated herein by reference.

The unified web thus formed has sufficient structural integrity to allow the web to be conveyed, transported, or otherwise handled.

The fibers form an open network of macropores; which macropores are defined by the openings between fibers. The web is characterized as having open cells. The cells are random in size and orientation through the length and depth of the web. The cell structures are generally formed of substantially nonlinear fibers that randomly intersect. The fibers are generally nonlinear between their points of contact or bonding. The web generally has a high void volume, e.g., 40 to 99%, preferably 80% to 99%. The web is typically a substantially planar web wherein the pores or "open spaces" are uniformly distributed throughout the thickness of the web.

The staple fiber webs may comprises various functional additives including for example, antimicrobial coatings, ion capturing coatings, desiccants, and odor control particles.

The basis weight of the web is typically at least 100 gsm, 125 gsm, or 150 gsm and typically no greater than 800 gsm. In some embodiments, the web has a basis weight no greater than 550 gsm, 500 gsm, 450 gsm, 400 gsm, or 350 gsm, or 300 gsm.

The web typically has a thickness of at least 3 or 4 mm to about 20 mm. In some embodiments, the web has a thickness is no greater than 15, 14, 13, 12, 11 or 10 mm.

The density of the web is typically at least about 0.01 g/cm$^3$ and no greater than about 0.10 g/cm$^3$. In some embodiments, the web has a density no greater than 0.06 g/cm$^3$, 0.05 g/cm$^3$, 0.04 g/cm$^3$, or 0.03 g/cm$^3$. The web may have a density of at least 0.01 g/cm$^3$, 0.015 g/cm$^3$, or 0.02 g/cm$^3$.

The staple fiber web preferably exhibits sufficient flexibility, which can be amenable to increased comfort when such web is utilized as a fluid transport element of an assembled intermediate or (e.g. disposable) absorbent article. One property that is indicative to flexibility is work of compression; i.e. the total area under a stress-strain curve (between 0-90 kPa). Work of compression is an indicator of the energy absorbing properties of a material as calculated according to the formula described in US2008/0001431; incorporated herein by reference. The web typically exhibits a work of compression of no greater than 20 kJ/m$^3$. In some embodiments, the web exhibits a work of compression of no greater than 15 kJ/m$^3$ or 10 kJ/m$^3$. The work of compression of the web is typically at least 2 or 3 kJ/m$^3$. In some embodiments, the work of compression is no greater than 9 or 8 kJ/m$^3$.

The webs are typically non-wicking. Although the fluid does not wick (i.e. travel vertically), the staple fiber web can retain fluid, resulting in a weight gain during testing. For example, the nonwoven web may exhibit a vertical wicking of saline solution of no greater than 5, 4, 3, 2, or 1 mm. Such vertical wicking is a property of the web alone, in the absence of being proximate an absorbent material. Without intending to be bound by theory, it is surmised that the web is non-wicking due to the fibers being spaced too far apart to create capillary action. The non-wicking webs exemplified herein are generally prepared from a hydrophobic polymer such as a polyolefin. Further, such non-wicking webs are free of hydrophilic (e.g. cellulose) fibers and superabsorbent polymer.

The webs were found to provide fast fluid transport rates (as tested in accordance to the test method described in the examples). Such fluid transport rate is also a property of the web alone, in the absence of being proximate an absorbent material. In some embodiments, the fluid transport rate was no greater than 15, 14, 13, 12, 10, 9, 8, 7, 6, 5, 4, or about 3 seconds with a weight of 4 kg. In some embodiments, the fluid transport rate was no greater than 30 seconds and in some embodiments no greater than 30, 25, 20, 10, or about 5 seconds with a weight of 12 kg. In some embodiments, the fluid transport rate was no greater than 60, 55, 50, 40, 30, or about 10 seconds with a weight of 24 kg.

The staple fiber webs described herein are suitable for use as a fluid transport component of an assembled intermediate, such as suitable for use in a (e.g. disposable) absorbent personal hygiene article. Whereas a finished personal hygiene article typically comprises a fluid transport nonwoven web proximate an absorbent (e.g. core) material between a fluid pervious topsheet and fluid impervious backsheet, an assembled intermediate article lacks at least one requisite component of a finished absorbent article. For example, the assembled intermediate typically lacks a fluid impervious backsheet and/or a fluid pervious topsheet. Thus, the assembled intermediate may be a component of a finished personal hygiene article.

The assembled intermediate comprises the staple fiber web, as described herein, in combination with at least one other substrate. In some embodiments, the assembled intermediate comprises the staple fiber web proximate, but not bonded to another substrate. For example, the web may be placed proximate an absorbent material forming an assembled intermediate during the manufacture of an absorbent article. In other embodiments, the assembled intermediate comprises the staple fiber web bonded to another substrate. For example, the web may be bonded to a (e.g. liquid pervious) carrier substrate, such as a nonwoven or tissue, to facilitate handling of the web by conventional high speed manufacturing processing. In yet another embodiment, the staple fiber web alone or in combination with a proximate absorbent material may be coated with a (e.g. pressure sensitive) adhesive on at least one major surface that is covered by a release liner carrier substrate. During manufacture of an absorbent article, the release liner is removed and the adhesive is contacted with another component of an absorbent article, such as a liquid impervious backsheet. In yet another embodiment, the staple fiber web in combination with a proximate absorbent material may be bonded to a carrier substrate such as a nonwoven or film that may subsequently be cut into pieces for and incorporation into an absorbent article.

Figure 12:
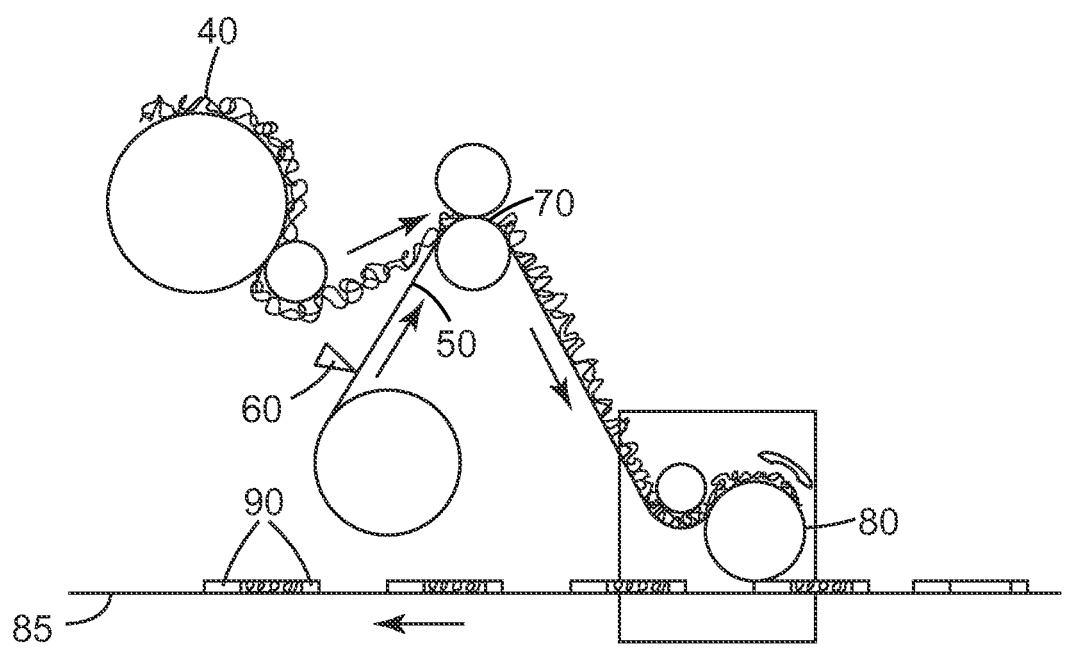
FIG. 12 is a schematic of an embodiment of an apparatus that can be used to further fabricate a staple fiber web into an assembled intermediate or article.

FIG. 12 depicts one illustrative method of a staple fiber nonwoven web being fabricated into an assembled intermediate. With reference to FIG. 12, the staple fiber web 40 may be conveyed to an apparatus 80 that cuts the web into discrete pieces and places them proximate an absorbent material 90. The assembled intermediate of the staple fiber web proximate the absorbent material may be conveyed on a moving belt 85 that conveys the assembled intermediate to subsequent manufacturing operation. Alternatively, the assembled intermediate may be temporarily or permanently bonded to a carrier substrate provided on the belt. When bonded to a carrier substrate, such intermediate may be wound on a roll, to be utilized as a component of an absorbent article. The staple fiber web may be bonded to another substrate, such as a liquid pervious substrate 50 (e.g. nonwoven, tissue, or fluid acquisition layer). This can be accomplished for example by applying an adhesive to the substrate 50 with an applicator 60 and laminating the adhesive applied substrate to the web 40 in a laminating nip 70, as further depicted in FIG. 12. Alternatively or in combination with a liquid pervious substrate (e.g. nonwoven, tissue, or fluid acquisition layer) being applied to (the upper, topsheet-facing) major face of the web; a substrate may be bonded to the opposing (lower, backsheet-facing) major surface of the web. The inclusion of a substrate, such as tissue, can aid in handling the web in subsequent operation. The inclusion of a substrate, such as tissue, can also aid in the web being cut into discrete pieces for inclusion into the finished composite absorbent constructions using a vacuum wheel type applicator, which is a common and known way of cutting and placing discrete pieces of material onto another material. In the absence of the tissue or other layer to reduce the porosity and air flow of the web, it may be difficult to handle the web using vacuum assisted cutting and placing operations.

When being bonded to another substrate, the staple fiber web or more typically the other substrate can be coated with an adhesive or binder on all or a portion of its surface area. Examples of suitable emulsion, hot melt, curable, or solvent-based adhesives or binders or pressure sensitive adhesives include (meth)acrylate-based pressure sensitive adhesives, such as those described in U.S. Pat. No. Re 24,906 (Ulrich), polyurethane adhesives, natural or synthetic rubber-based adhesives, epoxy adhesives, curable adhesives, phenolic adhesives, and the like.

The staple fiber nonwoven webs described herein are suitable for use as a fluid transport component of other absorbent articles, such as suitable for spill containment or medical uses, such as wound dressings. Such other absorbent articles may comprise all the requisite components of a finished (e.g. disposable) absorbent article. Hence, such other articles may comprise a fluid transport nonwoven web proximate an absorbent (e.g. core) material in combination with a fluid pervious topsheet and/or a fluid impervious backsheet.

The staple fiber nonwoven webs were found to provide fast fluid (e.g. saline solution) uptake rates when proximate an absorbent material. By proximate it is meant that at least a portion of the nonwoven web is in direct contact with the absorbent material or that a portion of the nonwoven web is in fluid communication with the absorbent material, yet not in direct contact. When the nonwoven web is in fluid communication, but not in direct contact, one or more other fluid pervious substrates, such as a tissue layer, may be present between the nonwoven web and absorbent material. In some favored embodiments, the nonwoven web comprises a first major face and a second opposing major face substantially parallel to the first major face and a thickness in a direction orthogonal to the first and second major face. The thickness of nonwoven web defines lateral edges and the absorbent material is in contact with or in fluid communication with at least a portion of the lateral edge. In some embodiments, at least two opposing lateral edges of the nonwoven web are in contact with or in fluid communication with the absorbent material. The other two opposing edges may be fluid impervious by sealing such edges. In another embodiment, all the lateral edges of the nonwoven web are in contact with the absorbent material.

The absorbent (core) material is typically a highly absorbent material that comprises superabsorbent polymer. The absorbent material typically comprises a blend of cellulosic fibers and superabsorbent material. One illustrative absorbent material has a basis weight from about 100 $g/m^2$ to about 700 $g/m^2$ which has been air-laid as a bottom layer of pulp, a middle layer of pulp and superabsorbent polymer disposed in amongst the pulp, and a top layer containing at least some pulp. The absorbent material may have a density of 0.25 or 0.3 g/cc to about 0.4 g/cc.

The absorbent material typically comprises at least 5 or 10 wt-% and preferably at least 15, 20, 25 or 30 wt-% of superabsorbent polymer. The superabsorbent polymer is typically no greater than 60 wt-% of the absorbent material and in some embodiments, no greater than 55, 50, 45, or 40 wt-%. The absorbent material may have a basis weight of at least 150 to 200 $g/m^2$ and typically no greater than 300 or 350 $g/m^2$.

Various absorbent (core) materials and methods of making such have been described in the art. (See for example U.S. Pat. No. 4,610,678 and U.S. Pat. No. 6,896,669)

In some embodiments, the fluid uptake rate (as measured in accordance with the test method described in the examples) was no greater than 10, 9, 8, 7, 6, or about 5 seconds with a weight of 4 kg. Notably a commercially available product that was tested was found to have a fluid uptake rate of about 23 seconds with a weight of 4 kg. In some embodiments, the fluid uptake rate was no greater than 50, 40, 30, 20, or 15 seconds with a weight of 12 kg. Notably a commercially available product that was tested was found to have a fluid uptake rate of about 98 seconds with a weight of 12 kg. Such fluid uptake performance can be achieved with a single fluid challenge (100 ml of 0.9% NaCl in water) or at least two (2-100 ml doses of 0.9% NaCl in water separated by a time interval of 2 minutes). Although the fluid uptake rate was measured on a finished personal hygiene article, the topsheet and backsheet are surmised to have little or no effect on the test results. Hence, the fluid uptake rate (as tested in accordance to the test method described in the examples) is surmised a property of an assembled intermediate of the staple fiber web proximate an absorbent material.

Another property that is indicative of the fluid transport properties of the staple fiber web is length of longitudinal fluid distribution (as tested in accordance to the test method described in the examples). In some embodiments, the length of longitudinal fluid distribution is at least 100, 110, 120, 130, 140, 150 or 160 mm with a weight of 4 kg. Notably a commercially available product that was tested was found to have a length of longitudinal fluid distribution of 85 mm. In some embodiments, the length of longitudinal fluid distribution is at least 100, 125, 150, 160, 170, 180, 190, or 200 mm with a weight of 12 kg. Notably a commercially available product that was tested was found to have a length of longitudinal fluid distribution of 85 mm.

The staple fiber web, such as when utilized as a fluid transport element of an assembled intermediate, can have various shapes including symmetrical (having a point, line, or plane of symmetry) or unsymmetrical shapes. The shape of the webs is envisioned to include but are not limited to circles, ovals, squares, rectangles, pentagons, hexagons, octagons, trapezoids, truncated pyramids, hourglasses, dumbbells, dog bones, etc. The edges and corners can be straight or rounded. The sides can be curved (convex or concave), tapered, flared, or angled. In addition, the web can contain cut-out regions that create voids, cavities, depressions, channels, or grooves. In some embodiments, the shape of the web is preferably rectangular. Regardless of the shape, the staple fiber web fluid transport elements can generally be defined as having a first major face, a second opposing major face substantially parallel to the first major face, and a thickness in a direction orthogonal to the first and second major face.

The staple fiber web may comprise various functional additives including for example, antimicrobial coatings, ion capturing coatings, desiccants, and odor control particles.

There are various ways in which the web can be utilized as a fluid transport element proximate an absorbent material, some of which are depicted in FIGS. 1-9, as will subsequently be described. In some favored embodiments, the thickness of the staple fiber web defines lateral edges that are at least partially in fluid communication with the absorbent material. In some embodiments, the lateral edges of the staple-fiber web are in fluid communication with the absorbent material by direct contact. In other embodiments, a low absorbency layer (i.e. lacking superabsorbent polymer), such as a tissue layer, may be present between the lateral edges of the staple fiber web and the absorbent material.

In some favored embodiments, the staple fiber web is inserted within an absorbent material such that substantially all the lateral edges are in fluid communication with the absorbent material. This arrangement can have faster fluid uptake. However, the length of longitudinal fluid distribution may be less. In yet other embodiments, at least two opposing lateral edges of the nonwoven web are in contact with the absorbent material. For example the lateral edges at the end-portion of the staple fiber web may be in contact with the absorbent material. If the staple fiber web is rectangular shaped, the end portions correspond to the lateral peripheral edges that define the width and typically a portion of the length. However, two opposing lateral peripheral edges along the length of the central-portion of the staple-fiber web may be rendered fluid impervious for example by sealing the edge or by including a fluid impervious film between such lateral edges and the adjacent absorbent material, as will further be explained with reference to FIG. 7. This arrangement can have slower fluid uptake. However, the length of longitudinal fluid distribution may be greater.

The assembled intermediate comprising the staple fiber web (fluid transport element) proximate absorbent material may further comprise another substrate prior to incorporation into a (e.g. disposable) absorbent article. Common substrates that are often included in a (disposable) absorbent article include topsheets, acquisition distribution layers (ADLs), and backsheets.

The topsheet is typically compliant, soft feeling, and non-irritating to the wearer's skin. Further, the topsheet is liquid pervious, permitting liquids to readily penetrate through its thickness. Suitable topsheets may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. The topsheet is typically a hydrophobic material to isolate the wearer's skin from liquids in the absorbent material.

There are a number of manufacturing techniques which may be used to manufacture the topsheet. The topsheet may be woven, non-woven, spunbonded, carded, or the like. An illustrative topsheet is carded, and thermally bonded (1.5 denier polypropylene staple fibers). The topsheet may have a basis weight from about 18 to about 25 grams per square meter. Further, the topsheet typically has a minimum dry tensile strength of at least about 400 grams per centimeter in the machine direction and a wet tensile strength of at least about 55 grams per centimeter in the cross machine direction. An acquisition distribution layer (also sometimes called a "surge" layer) is typically disposed beneath the topsheet and over the absorbent core. Acquisition layers have typically been constructed of a woven, non-woven or carded fibrous material. They are arranged to quickly absorb the liquid through the absorbent article's top sheet for temporary retention (e.g., to act as a temporary reservoir), and to transfer that liquid into the underlying absorbent core at a rate at which the core can absorb for final or permanent retention. The acquisition layer typically improves "wicking" of the absorbent article by spreading the body fluid in the "x" and "y" plane over the area of the core encompassed by the acquisition layer while also carrying the fluid in the "z" direction to the absorbent core. Examples of commercially available materials used for acquisition layers in disposable absorbent articles are through-air bond staple fibers, adhesively bonded staple fibers, and thermally point bonded staple fibers.

The backsheet is impervious to liquids and typically is a thin plastic film, although other liquid impervious materials may also be used. The backsheet is typically flexible, meaning that it is compliant and will readily conform to the general shape and contours of the wearer's body. The backsheet prevents the exudates absorbed and contained in the absorbent material from wetting articles which contact the absorbent article such as bed sheets and undergarments. One illustrative backsheet is polyethylene film having a thickness of from about 0.012 mm (0.5 mil) to about 0.051 centimeters (2.0 mils). The backsheet may be embossed and or matte finished to provide a more clothlike appearance. Further, the backsheet may permit vapors to escape from the absorbent member while still preventing exudates from passing through the backsheet.

In a typical disposable absorbent article, the topsheet and backsheet are associated together in any suitable manner. Typically, the topsheet and the backsheet are affixed directly to each other at the periphery of the article by an attachment means such as an adhesive or any other attachment means as known in the art.

FIG. 1 depicts a top view of an illustrative absorbent article 200 comprising an assembled intermediate of a staple fiber web fluid transport element 260 proximate an absorbent (e.g. core) material 280. Absorbent article 200 further comprises a fluid pervious topsheet 220, a fluid pervious acquisition distribution layer (ADL) 240 beneath and in fluid communication with the top sheet 220, and a staple fiber web fluid transport element 260 beneath and in fluid communication with the ADL. The absorbent (e.g. core) material 280 typically surrounds the fluid transport element 260.

Figure 2:
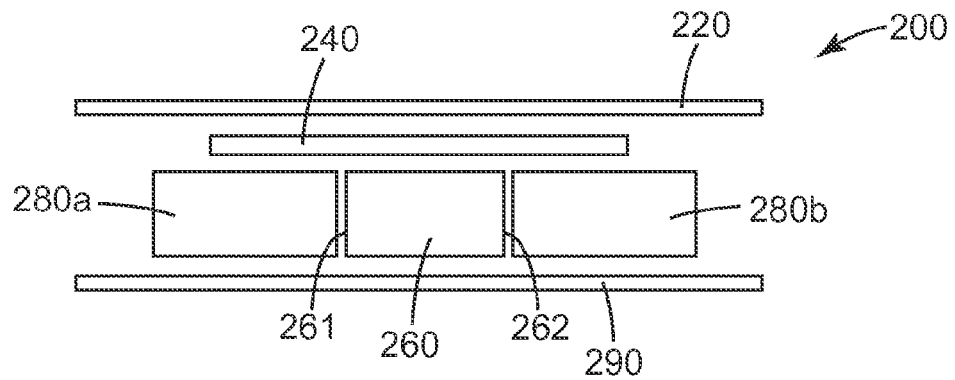
FIG. 2 is a cross-sectional view of the absorbent article of FIG. 1.
Figure 11:
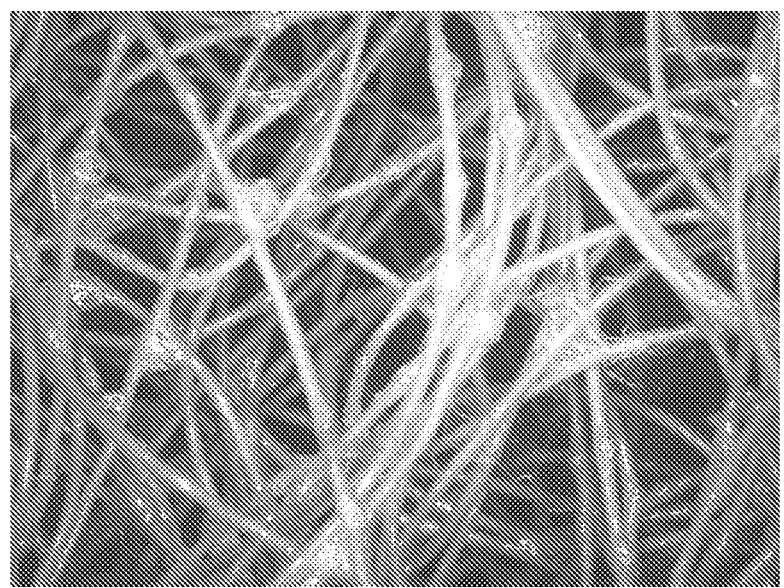
FIG. 11 is a microphotograph of an embodied staple fiber nonwoven web.

FIG. 2 is a central cross-sectional view of the illustrative assembled intermediate and absorbent article of FIG. 11. Staple fiber web fluid transport element 260 comprises lateral edge 261 in fluid communication, such as by direct contact with absorbent (core) portion 280a and lateral edge 262 in fluid communication, such as by direct contact, with absorbent (core) portion 280b.

FIGS. 3-6 and FIG. 9 depict cross-sectionals views of other illustrative assembled intermediates, comprising a fluid transport element (360, 460, 560, 660, and 860) proximate an absorbent material (380, 480, 580, 680 and 880), incorporated into an absorbent article. In each of the cross-sectional views of FIGS. 3-6 and FIG. 9, the thickness of the staple fiber web fluid transport element defines lateral edges (361, 362; 461, 462; 561, 562; 661, 662; 861,862) and the lateral edges are in fluid communication, such as by being in direct contact with the absorbent material.

In the illustrative embodiments of FIG. 2, FIGS. 4-6 and FIG. 9, the opposing major face of the staple fiber web fluid transport element (260, 460, 560, 660, and 860) is in direct contact with fluid impervious backsheet element (290, 490, 590, 690, 890). A tissue layer (not shown) may optionally be present between the fluid impervious backsheet element (290, 490, 590, 690, 890) and staple fiber web fluid transport element (260, 460, 560, 660, and 860). Such tissue can be attached directly to the fluid transport element to aid in handling. In the embodiments depicted in FIG. 2, FIGS. 4-6 and FIG. 9; a highly absorbent (core) material (i.e. comprising super absorbent polymer) is not present between the fluid impervious backsheet element (290, 490, 590, 690, 890) and staple fiber web fluid transport element (260, 460, 560, 660, and 860).

Figure 3:
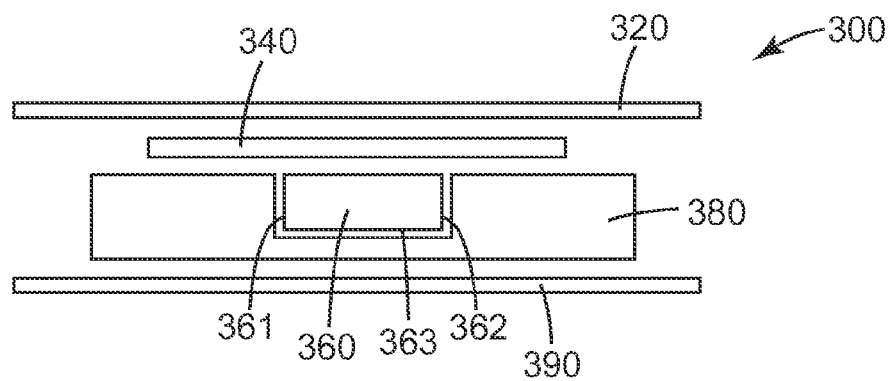
FIGS. 3-7 are cross-sectional views of other absorbent articles.

FIG. 3 is a central cross-sectional view of another illustrative assembled intermediate incorporated into absorbent article 300. This embodiment comprises a fluid pervious topsheet 320, a fluid pervious acquisition distribution layer (ADL) 340 beneath and in fluid communication with the top sheet 320, and a staple fiber web fluid transport element 360 beneath and in fluid communication with the ADL. Staple fiber web fluid transport element 360 comprises lateral edges 361 and 362 in fluid communication, such as by direct contact with absorbent (core) material 380. Unlike the embodiments depicted in FIG. 2, FIGS. 4-6 and FIG. 9; in this embodiment, opposing (bottom) major face 363 of staple fiber web fluid transport element 360 is in contact with absorbent core material 380. Thus, a layer of highly absorbent (core) material 380 is present between the liquid impervious backsheet 390 and staple fiber web fluid transport element 360. In this embodiment, the surface area of the staple fiber web fluid transport element 360 in fluid communication with absorbent core material 380 can be greater than FIG. 2 for example.

Figure 4:
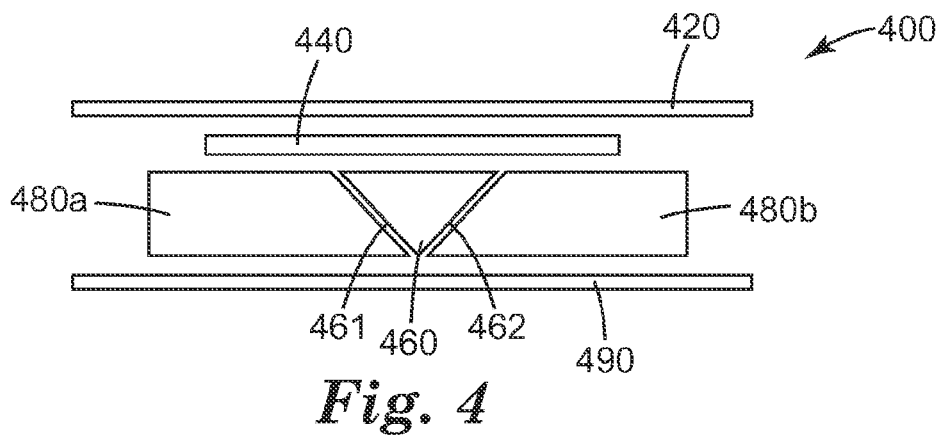

FIG. 4 is a central cross-sectional view of another assembled intermediate incorporated into illustrative absorbent article 400. This embodiment comprises a fluid pervious topsheet 420, a fluid pervious acquisition distribution layer (ADL) 440 beneath and in fluid communication with the top sheet 420, and a staple fiber web fluid transport element 460 beneath and in fluid communication with the ADL. Staple fiber web fluid transport element 460 comprises lateral edge 461 in fluid communication with absorbent material portion 480a and lateral edge 462 in fluid communication with absorbent material portion 480b, such as by direct contact with absorbent (core) material 480. In this embodiment, the staple fiber web fluid transport element 460 has a triangular shaped cross-section with one of the apexes of the triangle in contact with liquid impervious backsheet 490. In this embodiment, the surface area of lateral edges 461 and 462 of staple fiber web fluid transport element 460 can be greater than the surface area of the lateral edges of a staple fiber web having a rectangular cross section (such as shown in FIG. 2).

Figure 5:
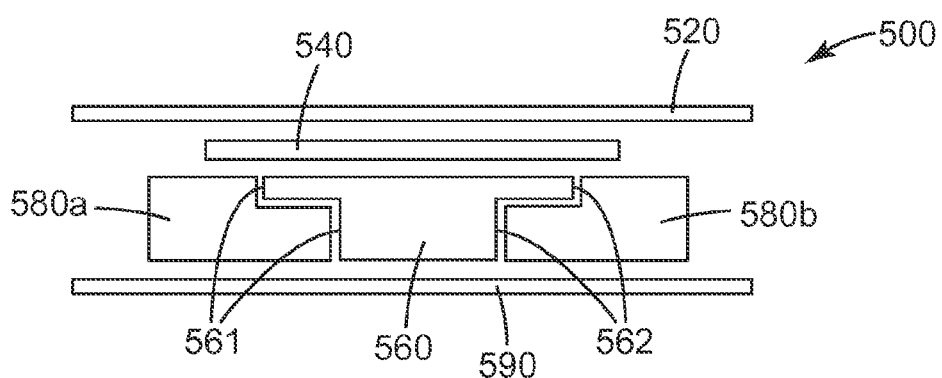

FIG. 5 is a central cross-sectional view of another illustrative assembled intermediate incorporated into absorbent article 500. This embodiment comprises a fluid pervious topsheet 520, a fluid pervious acquisition distribution layer (ADL) 540 beneath and in fluid communication with the top sheet 520, and a staple fiber web fluid transport element 560 beneath and in fluid communication with the ADL. Staple fiber web fluid transport element 560 comprises lateral edges 561 and 562 in fluid communication with absorbent material portions 580a and 580b respectively, such as by direct contact with absorbent (core) material 580. In this embodiment, the staple fiber web fluid transport element 560 has a T-shaped cross-section with the bottom surface in contact with backsheet 590.

Figure 6:
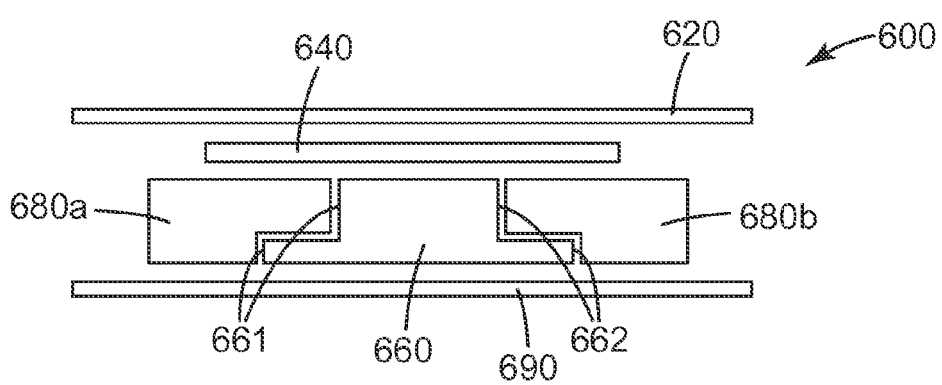

FIG. 6 is a central cross-sectional view of another illustrative assembled intermediate incorporated into absorbent article 600. This embodiment comprises a fluid pervious topsheet 620, a fluid pervious acquisition distribution layer (ADL) 640 beneath and in fluid communication with the top sheet 620, and a staple fiber web fluid transport element 660 beneath and in fluid communication with the ADL. Staple fiber web fluid transport element 660 comprises lateral edges 661 and 662 in fluid communication with absorbent material portions 680a and 680b respectively, such as by direct contact with absorbent (core) material 680. In this embodiment, the staple fiber web fluid transport element 660 has an inverted T-shaped cross-section with the bottom surface in contact with backsheet 690.

Figure 7:
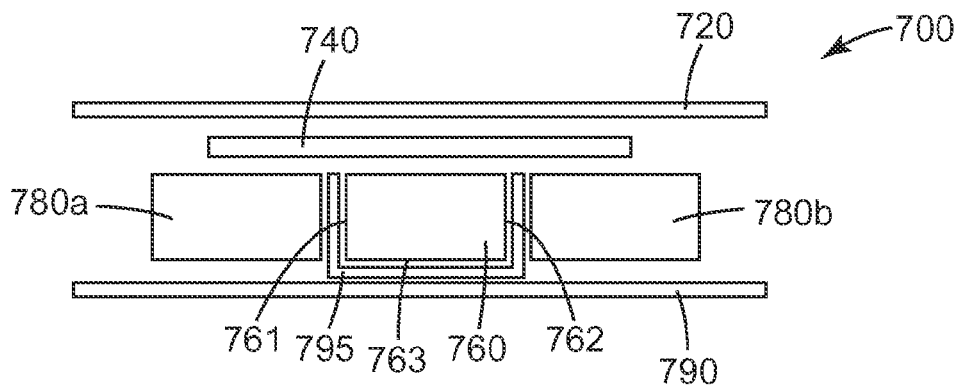

FIG. 7 is a central cross-sectional view of another illustrative assembled intermediate incorporated into absorbent article 700. This embodiment comprises a fluid pervious topsheet 720, a fluid pervious acquisition distribution layer (ADL) 740 beneath and in fluid communication with the top sheet 720, and a staple fiber web fluid transport element 760 beneath and in fluid communication with the ADL. Staple fiber web fluid transport element 760 comprises lateral edges 761 and 762 and bottom edge 763 in contact with a liquid impervious (e.g. film) layer 795 that envelopes the staple fiber web fluid transport element 760 on both lateral edges and the opposing (bottom) surface. In some embodiments, this liquid impervious (e.g. film) layer has the same length as the fluid transport nonwoven web. In other embodiments, this liquid impervious (e.g. film) layer may have a shorter length and only present at the central region (about 50%) of the article. In this embodiment, the article at the end portions of the fluid transport nonwoven web (in cross-section) may have the same appearance as FIG. 2.

Figure 8:
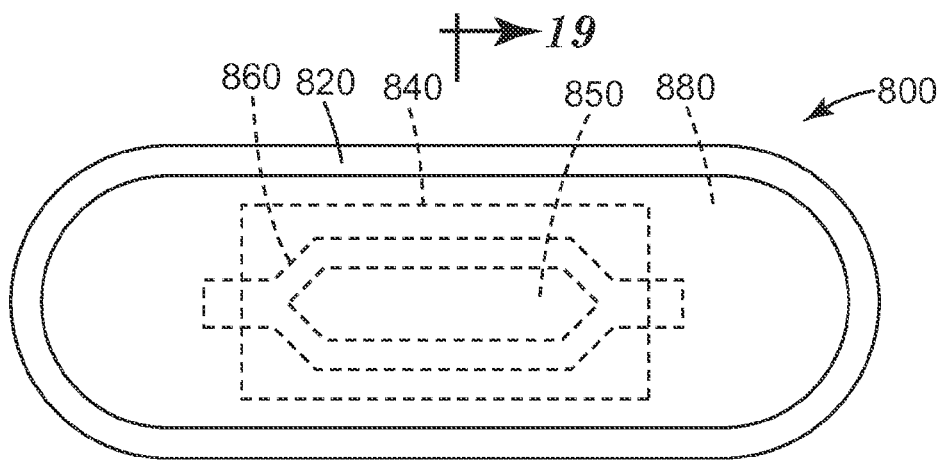
FIG. 8 is a top view of another absorbent article.

FIG. 8 depicts a top view of another illustrative assembled intermediate incorporated into absorbent article 800 comprising a fluid pervious topsheet 820, a fluid pervious acquisition distribution layer (ADL) 840 beneath and in fluid communication with the top sheet 820, and a staple fiber web fluid transport element 860 beneath and in fluid communication with the ADL. The absorbent (e.g. core) material 880 typically surrounds the fluid transport element 860.

Figure 9:
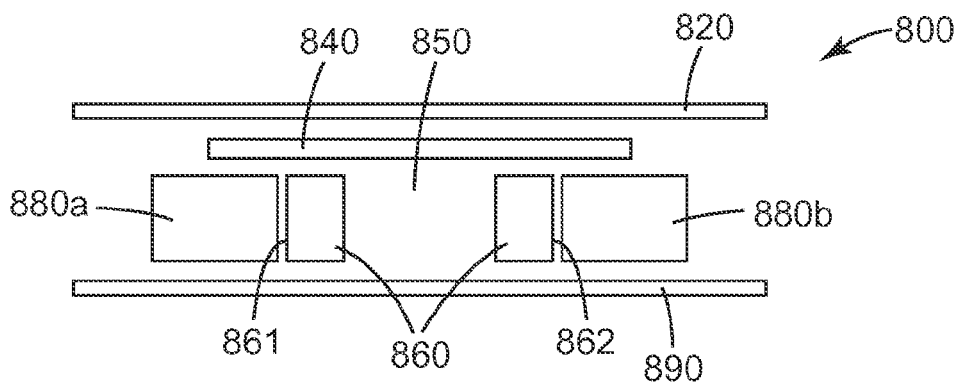
FIG. 9 is a cross-sectional view of the absorbent article of FIG. 8.
Figure 10:
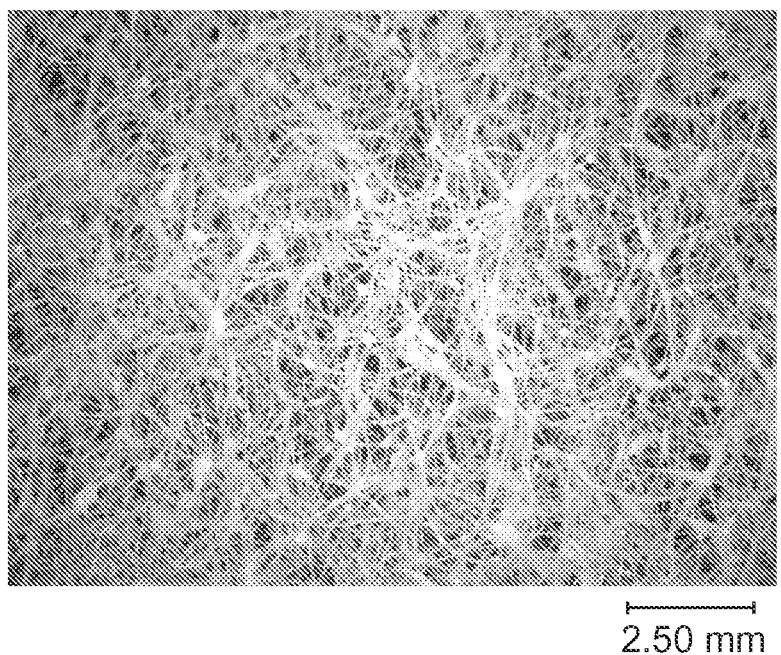
FIG. 10 is a microphotograph of an embodied staple fiber nonwoven web.

FIG. 9 is a central cross-sectional view of assembled intermediate and absorbent article of FIG. 8. As best shown in shown in FIG. 9, this embodiment further comprises a void 850 (an air-space). The staple fiber web fluid transport element 860 is typically sufficiently resilient such that the air-space is maintained with moderate compression.

In some embodiments, the fluid transport element (e.g. 260 of FIG. 1) has a dimension (e.g. length) that extends beyond the length (i.e. longest dimension) of the ADL. In such embodiment, the fluid transport element may also be in fluid communication such as by direct contact with the topsheet. Alternatively, the dimension of the fluid transport element 260 may be selected such that the first major face of fluid transport element 260 is in contact with the ADL and not with the topsheet.

The assembled intermediates or absorbent articles may further comprise one or more tissue layers between the ADL and fluid transport element. Such tissue layers are typically not "highly absorbent" as in the case of the absorbent (e.g. core) material comprising superabsorbent polymer.

The invention is illustrated by the following non-limiting examples.

Nonwoven Web Preparation

Examples 1-3

The nonwoven webs of Examples 1-2 were prepared by blending about 80% by weight of 15 denier polyethylene terephthalate (PET) staple fibers (36 mm cut length, 10 crimps per inch) with about 20% by weight of 6 denier PET staple fibers (42 mm cut length, 10 crimps per inch). In a continuous web forming process the nonwoven web was air-laid using a Rando Webber machine (commercially available from Rando Machine Corporation, Macedon, N.Y.). Polyurethane binder was applied to the web through a gravure coating process and the binder coated web was dried and cured by passing the web first through a hot air oven set at 143° C. and then through a hot air oven set at 171° C. The average polyurethane dried coat weight was 86 gsm for Example 1 and 146 gsm for Example 2.

The nonwoven web of Example 3 was prepared from a 3-dimensional spiral crimped PET staple fiber having an average fiber diameter of 250 microns and a cut length of 150 mm (available from the Enkev Company, Volendam, Netherlands). The fiber was formed in the shape of a spiral spring having a diameter of about 10 mm and a length of about 20 mm. In a continuous web forming process the nonwoven web was air-laid using a SPIKE machine (commercially available from FormFiber NV, Hasselager, Denmark). Details of the SPIKE machine and methods for using the SPIKE machine in forming air-laid webs is described in U.S. Pat. Nos. 7,491,354 and 6,808,664. Polyurethane binder was applied to one face of the web using air spray guns. The adhesive coated web was dried and cured by passing through a hot air oven set at 135° C. to provide an average dry binder coat weight of 150 gsm. The web was then conveyed through a calendaring oven set at 135° C. The formed web was flipped and polyurethane binder was applied to the opposite face of the web using air spray guns. The process of drying, curing, and calendaring the binder coated web as described above was repeated resulting in the second polyurethane coating being applied at an average dry coat weight of 150 gsm.

In Table 1, the measured values of average fiber diameter (microns), web basis weight (gsm), web thickness (mm), and web density (g/cm$^3$) are reported for Examples 1-3.

TABLE 1

Air-Laid Nonwoven Webs

|  | Average Fiber Diameter (microns) | Web Basis Weight (gsm) | Web Thickness (mm) | Web Density (g/cm$^3$) |
|---|---|---|---|---|
| Example 1 | 40 | 184.2 | 8.0 | 0.023 |
| Example 2 | 40 | 276.4 | 10.0 | 0.028 |
| Example 3 | 250 | 614.0 | 11.4 | 0.054 |

Compressibility

The energy required to compress the webs was measured. All testing was conducted at constant temperature (23° C.±2° C.) and relative humidity (50%±5%). All materials and equipment were equilibrated at these conditions for a minimum of 24 hours prior to testing. A universal constant rate of extension tensile testing instrument equipped with a computer for data recording and the required load ranges was used (Series 4200, 4500, or 5500 available from Instron Engineering Corporation, Canton, Mass.). The instrument crosshead speed was set to 200 mm/minute and the calibrated load cell used was rated for 500 N. The finished sample of nonwoven web was cut in a 3 inch diameter circle and the thickness was measured using a digital hand-held caliper. Three replicates of fresh materials were used for each sample and the data is reported as the average of the recorded values.

The Instron instrument was fitted with two compression platens (6 inch diameter) aligned in parallel with one attached to the lower jaw creating the base and one attached to the upper jaw creating the moving piston that applied the compressive force. The platens were brought into contact and the jaw gap measurement was set to zero on the instrument. The platens were then drawn apart to a distance equal to the sample thickness. The gauge length was reset to zero and then manually jogged a nominal distance further apart to allow for sample placement. The sample was placed on the lower platen and the top platen was returned to the zero position against the sample. The sample was then compressed with automatic recording of the compressibility (percent strain) at compressive stresses (kPa) of 1, 5, 10, 20, 40, 60, and 100 kPa (Table 2). The area under the plotted stress-strain curve (between 0–90 kPa) was calculated and reported as the Work of Compression (WOC) in kilojoules/m$^3$.

TABLE 2

Compressibility Data for Air-Laid Nonwoven Webs

| | Percent Strain (%) | | | | | | | |
|---|---|---|---|---|---|---|---|---|
| Example | at 1 kPa | at 5 kPa | at 10 kPa | at 20 kPa | at 40 kPa | at 60 kPa | At 100 kPa | WOC (kJ/m$^3$) |
| Example 1 | 21.8 | 54.5 | 71.3 | 84.0 | 90.5 | 93.1 | 96.0 | 7.3 |
| Example 2 | 26.1 | 62.4 | 77.2 | 87.4 | 92.3 | 94.4 | 96.8 | 8.6 |
| Example 3 | 13.7 | 49.2 | 59.2 | 67.9 | 74.2 | 77.6 | 81.5 | 15.2 |

Vertical Wicking

A shallow aluminum tray was filled with saline solution (0.9% NaCl in water) to a depth of 12.7 mm. To enhance visualization, the saline solution was dyed with red food coloring. Test samples of Example 1 and Comparative Examples A1-A3 were prepared as 25.4 mm by 152.4 mm strips. Comparative Example A1 was the acquisition distribution layer (ADL) obtained from a size six baby diaper commercially available from the Kimberly Clark Corporation, Neenah, Wis., under the trade designation "HUGGIES LITTLE MOVERS". The ADL was a 3 mm thick nonwoven web having an average basis weight of 106 gsm and an average fiber diameter of 30 microns. Comparative Example A2 was the absorbent core obtained from an adult incontinence pad commercially available from the SCA Personal Products, Philadelphia, Pa., under the trade designation "TENA SERENITY". The absorbent core was a bonded, air-laid material containing cellulosic fibers and superabsorbent polymer layered between two sheets of tissue. The absorbent core was 5 mm thick and had an average basis weight of 440 gsm. Comparative Example A3 was a "WYP-ALL L30" nonwoven tissue commercially available from the Kimberly Clark Corporation. A clip was attached to the narrow end of each sample and the samples were individually hung from a support located above the tray. The samples were oriented so that they were positioned perpendicular to the tray and were submerged into the saline solution so that the free ends of the samples touched the bottom of the tray. The samples were maintained in the saline solution for 60 minutes at ambient temperature. The samples were removed from the saline solution and the distance of travel by the saline solution in each sample was measured with a ruler (Table 3). The samples were subsequently drip dried by suspending in air for five minutes and then weighed. The percent weight gain from the fluid held by the web is reported in Table 3.

TABLE 3

| | Distance of Travel by the Saline Solution (mm) | Percent Weight Gain |
|---|---|---|
| Example 1 | 0.0 | 300% |
| Comparative Example A1 | 9.5 | 121% |
| Comparative Example A2 | 76.2 | 912% |
| Comparative Example A3 | 127 | 450% |

Fluid Transport Rate

The rates of fluid transport by the nonwoven webs of Examples 1-3 were measured with and without an applied compression force. A circular sample of the nonwoven web (75 mm diameter) was placed between two plexiglass plates (20.3 cm by 20.3 cm). A 15 mm diameter hole was cut through the center of the top plate. A glass, conical-shaped funnel (13 mm inner diameter stem) was positioned in the hole so that the bottom of the funnel stem was aligned flush with the bottom of the top plate. A minimum amount of Parafilm™ M (Pechiney Plastic Packaging, Chicago, Ill.) was wrapped around the stem in order to achieve a tight, non-leaking seal between the funnel stem and the hole in the plate. The top plate with attached funnel weighed 427 g. The nonwoven web sample was positioned so that the hole in the top plate was positioned directly above the center of the nonwoven web sample. To provide a compression force, individual weights were added to the top plate in a pattern that provided for an even distribution of the total weight (ranging from 0-24 added kilograms) on the top surface. The rate of fluid transport by the webs under different compression forces (0-24 kg) was determined by quickly adding a saline solution (100 mL of 0.9% NaCl in water) to the funnel and measuring the time required for all of the fluid to enter the web. To enhance visualization, the saline solution was dyed with red food coloring. The results for the web samples prepared from Examples 1-3 are presented in Table 4.

TABLE 4

| | Fluid Transport Rate (seconds) with Weight Added (kg) | | | | | | | |
|---|---|---|---|---|---|---|---|---|
| | 0 kg | 1 kg | 4 kg | 8 kg | 12 kg | 16 kg | 20 kg | 24 kg |
| Example 1 | 2 | 3 | 8 | 14 | 20 | 22 | 27 | 32 |
| Example 2 | 3 | 4 | 10 | 20 | 27 | 34 | 42 | 53 |
| Example 3 | 2 | 2 | 3 | 4 | 4 | 7 | NT | 7 |

NT = not tested

Fluid Uptake Rate and Fluid Distribution in Adult Incontinence Pads

The test apparatus and test method described above to measure the fluid transport rate of web samples was used to measure the fluid uptake rates and the fluid distribution of adult incontinence pads that were modified by replacing a section of the absorbent core of the pad with a sample of nonwoven web. A central portion of the entire thickness of the absorbent core was removed and the staple fiber web inserted in place of the removed absorbent core, such that one major face of the web was in contact with the topsheet or acquisition-distribution layer (ADL), the opposing major surface of the web was in contact with the backsheet, and the lateral edges corresponding to the thickness of the web were in contact with the absorbent core. Examples of adult incontinence pads used as test articles are well known to those skilled in the art and have been previously described in U.S. Pat. No. 5,019,065 (Scripps), U.S. Pat. No. 6,509,513 (Glaug), U.S. Pat. No. 4,834,735 (Alemany), and U.S. Pat. No. 4,610,678 (Weisman). A typical adult incontinence pad test article was composed of a top sheet; bottom sheet; absorbent core element located between the top and bottom sheets; and an optional ADL located between the absorbent core element and the top sheet. The edges of the top sheet and bottom sheet were attached to form a seal. The overall dimensions of the test pads ranged from about 26-31 cm (length) by 9-11 cm (width) by 3-10 mm (thickness). The overall weight of the test pads ranged from about 11-26 g.

The top sheet was a liquid permeable polypropylene nonwoven having a basis weight of about 27-37 gsm. The back sheet was a liquid impermeable polyethylene film having a thickness of about 0.5-2.0 mil. The absorbent core component was composed of a mixture of cellulosic fibers (about 70-80% by weight) and superabsorbent polymer (about 20-30% by weight). The dimensions of the absorbent core element ranged from about 24-29 cm (length) by 7-9 cm (width) by 3-10 mm (thickness). The amount of absorbent core in the pads ranged from about 8-25 grams. The amount of absorbent core removed to insert the nonwoven web ranged from about 1.5-3.5 g. In examples of pads with an inserted nonwoven web component, the pad was reassembled but the opened edge regions were not resealed. The optional ADL was a tissue or nonwoven layer with a basis weight of about 50-150 gsm. The dimensions of the ADL ranged from about 17-31 cm (length) by 4-8 cm (width).

The incontinence pad was positioned in the test apparatus so that the topsheet of the pad faced the upper plate (backsheet resting on the lower plate) and the pad was centered with respect to the hole in the top glass plate. The amount of saline solution used in each test was 75 mL.

The rate of fluid uptake by the pad under different compression forces (0-24 kg) was determined by quickly adding the saline solution to the funnel and measuring the time required for all of the fluid to enter the pad. The longitudinal distribution of the liquid in each pad was determined by removing the pad from the apparatus and measuring the total longitudinal distance (mm) traveled by the liquid in the pad. The leakage of liquid from the pads (grams) was measured by initially placing the entire test apparatus in a pan. Any liquid that leaked from the pad during the test was collected in the pan, recovered, and then weighed. The results are presented in Tables 5-7.

Example 4

A TENA SERENITY adult incontinence pad (available from SCA Personal Products, Philadelphia, Pa.) was modified by removing by hand a 30 mm by 120 mm portion of the absorbent core (centered both in the lateral cross section directions of the pad) and filling the subsequent void with a 1.1 g sample of Example 2. After filling the void, the pad was reassembled by repositioning the original top sheet and acquisition distribution layer of the pad. In this configuration, the fluid delivered from the funnel passed through the top sheet and the ADL before flowing into the inserted nonwoven web (only a negligible amount of fluid contacted the absorbent core without first contacting the nonwoven web). The web sample of Example 1 was reused for each of the test conditions. Between each test, the web sample was removed from a wet pad, dried by blotting, and then reinserted into the void of a fresh (dry) pad.

Example 5

A TENA SERENITY adult incontinence pad (available from SCA Personal Products, Philadelphia, Pa.) was modified by removing by hand a 30 mm by 120 mm portion of the absorbent core (centered both in the lateral cross section directions of the pad) and filling the subsequent void with a 2.9 g sample of Example 3. After filling the void, the pad was reassembled by repositioning the original top sheet and acquisition distribution layer of the pad. In this configuration, the fluid delivered from the funnel passed through the top sheet and the ADL before flowing into the inserted nonwoven web (only a negligible amount of fluid contacted the absorbent core without first contacting the nonwoven web). The web sample of Example 3 was reused for each of the test conditions. Between each test, the web sample was removed from a wet pad, dried by blotting, and then reinserted into the void of a fresh (dry) pad.

Comparative Examples B

Comparative Example B was an unmodified TENA SERENITY adult incontinence pad.

TABLE 5

| | Fluid Uptake Rate (seconds) with Weight Added (kg) | | | |
|---|---|---|---|---|
| | 0 kg | 1 kg | 4 kg | 12 kg |
| Example 4 | 3 | 4 | 5 | 12 |
| Example 5 | 2 | 4 | 6 | 16 |
| Comparative Example B | 4 | 6 | 23 | 98 |

TABLE 6

| | Length of Longitudinal Fluid Distribution in the Pad (mm) with Weight Added (kg) | | | |
|---|---|---|---|---|
| | 0 kg | 1 kg | 4 kg | 12 kg |
| Example 4 | 170 | 180 | 200 | 200 |
| Example 5 | 160 | 170 | 180 | 220 |
| Comparative Example B | 71 | 75 | 85 | 85 |

TABLE 7

| | Leakage of Liquid from the Pad (grams) with Weight Added (kg) | | | |
|---|---|---|---|---|
| | 0 kg | 1 kg | 4 kg | 12 kg |
| Example 4 | 0 | 0 | 0 | 0 |
| Example 5 | 0 | 0 | 0 | 0 |
| Comparative Example B | 9.1 | 0 | 0 | 0 |

What is claimed is:

1. An assembled intermediate consisting of a thermoplastic nonwoven web prepared from a hydrophobic polymer proximate an absorbent material; wherein the nonwoven web consists of a plurality of bonded staple fibers having an average diameter of 20 to 500 microns and the nonwoven web has a thickness of at least 3 mm ranging up to about 20 mm that defines lateral edges, a density ranging from 0.01 to 0.06 g/cm$^3$, and a work of compression no greater than 20 kJ/m$^3$; wherein the nonwoven web is free of hydrophilic fibers and superabsorbent polymer such that the nonwoven web exhibits a vertical wicking of saline solution of no greater than 5 mm; and the absorbent material is in contact with at least one lateral edge.

2. The assembled intermediate of claim 1 wherein the staple fibers have an average diameter of no greater than 200 microns.

3. The assembled intermediate of claim 1 wherein the nonwoven web has a work of compression of no greater than 15 kJ/m$^3$.

4. The assembled intermediate of claim 3 wherein the nonwoven web has a work of compression of no greater than 10 kJ/m$^3$.

5. The assembled intermediate of claim 1 wherein the nonwoven web has a basis weight ranging from 100 gsm to 400 gsm.

6. The assembled intermediate of claim 1 wherein the nonwoven web has a basis weight less than 300 gsm.

7. The assembled intermediate of claim 1 wherein the nonwoven web has a thickness no greater than 10 mm.

8. The assembled intermediate of claim 1 wherein the nonwoven web exhibits any one or combination of fluid transport rate properties selected from a fluid transport rate of no greater than 15 seconds with a weight of 4 kg;

a fluid transport rate of no greater than 30 seconds with a weight of 12 kg; and a fluid transport rate of no greater than 60 seconds with a weight of 24 kg.

9. The assembled intermediate of claim 1 wherein all the lateral edges of the nonwoven web are in contact with the absorbent material.

10. The assembled intermediate of claim 1 wherein the absorbent material comprises cellulosic fibers and superabsorbent polymer.

11. The assembled intermediate of claim 10 wherein the assembled intermediate exhibits any one or combination of fluid uptake rate properties selected from a fluid uptake rate of no greater than 10 seconds with a weight of 4 kg; and a fluid uptake rate of no greater than 30 seconds with a weight of 12 kg.

12. The assembled intermediate of claim 10 wherein the assembled intermediate exhibits any one or combination of length of longitudinal fluid distribution properties selected from a length of longitudinal fluid distribution of at least 100 mm with a weight of 4 kg; and a length of longitudinal fluid distribution of at least 100 mm with a weight of 12 kg.

13. The assembled intermediate of claim 11 where the assembled intermediate exhibits the fluid uptake property with one or two fluid challenges.

14. An absorbent article comprising the absorbent assembled intermediate of claim 1, wherein the article is not a personal hygiene article.

15. The assembled intermediate of claim 1 wherein openings between bonded staple fibers form an open network of macropores.

16. An assembled intermediate consisting of a thermoplastic nonwoven web prepared from a hydrophobic polymer proximate an absorbent material; wherein the nonwoven web exhibits a vertical wicking of saline solution of no greater than 5 mm, the nonwoven web consists of a plurality of bonded staple fibers having an average diameter of 20 to 500 microns wherein openings between bonded staple fibers form an open network of macropores, the nonwoven web has a density ranging from 0.01 to 0.06 g/cm$^3$, the nonwoven web has a work of compression no greater than 20 kJ/m$^3$, the nonwoven web has a thickness of at least 3 mm ranging up to about 20 mm that defines lateral edges, and the absorbent material is in contact with at least one lateral edge such that the nonwoven has a fluid transport rate of no greater than 15 seconds with a weight of 4 kg, and the nonwoven web is free of hydrophilic fibers and superabsorbent polymer such that the nonwoven web exhibits a vertical wicking of saline solution of no greater than 5 mm.

17. The absorbent article of claim 14 wherein the absorbent article is a wound dressing.

18. The absorbent article of claim 14 wherein the absorbent article is for medical use.

* * * * *